United States Patent [19]

Hjørnevik

[11] Patent Number: 6,137,005

[45] Date of Patent: *Oct. 24, 2000

[54] METHOD FOR MANUFACTURE OF PRODUCTS CONTAINING DISALTS OF FORMIC ACID

[75] Inventor: Leif Hjørnevik, Skien, Norway

[73] Assignee: Norsk Hydro ASA, Olso, Norway

[ * ] Notice: This patent issued on a continued prosecution application filed under 37 CFR 1.53(d), and is subject to the twenty year patent term provisions of 35 U.S.C. 154(a)(2).

[21] Appl. No.: 08/952,009

[22] PCT Filed: May 10, 1996

[86] PCT No.: PCT/NO96/00115

§ 371 Date: Feb. 26, 1998

§ 102(e) Date: Feb. 26, 1998

[87] PCT Pub. No.: WO96/35657

PCT Pub. Date: Nov. 14, 1996

[30] Foreign Application Priority Data

May 12, 1995 [NO] Norway ................................. 951885

[51] Int. Cl.$^7$ .................................................. C07C 53/06
[52] U.S. Cl. .............................................. 562/609
[58] Field of Search ............................................. 562/609

[56] References Cited

U.S. PATENT DOCUMENTS

| | | | |
|---|---|---|---|
| 1,650,984 | 11/1927 | Elod et al. .............................. | 562/609 |
| 4,261,755 | 4/1981 | Berry et al. ................................. | 106/90 |

FOREIGN PATENT DOCUMENTS

| | | |
|---|---|---|
| 85073 | 2/1958 | Denmark . |
| 0009366 | 4/1980 | European Pat. Off. . |
| 0241400 | 10/1987 | European Pat. Off. . |
| 292959 | 6/1916 | Germany . |
| 424017 | 6/1923 | Germany . |
| 1505388 | 3/1978 | United Kingdom . |

OTHER PUBLICATIONS

Berichte, vol. 36, 1903, E. Groschuff, "Neutral und saure Alkaliformiate. Studien über die Löslichkeit der Salze, XI" p. 1783–p. 1795.

Gmelins "Handbuch der anorganischen Chemie", 8.Ed System No. 21, Verlag Chemie G.M.B.H. Berlin 1928, pp. 816–819.

Gmelins "Handbuch der anorganischen Chemie", 8.Ed System No. 22, Verlag Chemie G.M.B.H. Berlin 1928, pp. 919–921.

Kendall et al., "Compound Formation and Solubility in Systems of the Type, Formic Acid: Metal Formate.", Journ. of Am. Chem. Soc. 1921, vol. 43, pp. 1470–1503.

*Primary Examiner*—Johann Richter
*Assistant Examiner*—Rosalynd Keys
*Attorney, Agent, or Firm*—Wenderoth, Lind & Ponack, L.L.P.

[57] ABSTRACT

A method for manufacture of products containing disalts of formic acid. Potassium hydroxide, carbonate, bicarbonate or formate, sodium hydroxide, carbonate, bicarbonate for formate, cesium hydroxide, carbonate, bicarbonate or formate or ammonium formate or ammonia is mixed with formic acid at 40–100° C., the mixture is cooled and centrifuged. The filtrate containing acid salt is collected. The filter cake is transported to a drier/mixer where other disalts, calcium formate and/or a desiccant can be added.

5 Claims, 2 Drawing Sheets

METHOD FOR MANUFACTURE OF PRODUCTS CONTAINING DISALTS OF FORMIC ACID

The present invention relates to a method for manufacture of products containing disalts of formic acid. The products are manufactured from potassium-, sodium-, ammonium- and cesium-compounds and formic acid containing 0–50% water in a reactor at 40–100° C.

It is often desired to have products with a high concentration of salts of monocarboxylic acids. Such products can be used for several purposes. In formate based animal feed additives, for instance, it is desired that the formate concentration is high and that the product does not emit acids, which act corrosively and may cause poor working conditions during manufacture and handling of the products.

In order to obtain such concentrated products, at least part of the mono salts of said acids can be substituted with disalts like diformate.

The mono salts of potassium, sodium, ammonium and cesium form disalts with monocarboxylic acids like for instance formic acid and acetic acid. The strength of the salt bonds decreases from cesium/potassium to ammonium. Potassium diformates are stable crystalline salts which decompose at temperatures above 120° C. The ammonium diformates are less stable than potassium diformate and the decomposition temperature of ammonium diformate is reported to be in the range 25–30° C. The sodium diformates decompose in the temperature range 100–120° C.

In Gmelins Handbuch der anorganischen Chemie, 8. Ed.System No. 21 and 22, Verlag Chemie G.M.B.H Berlin 1928, pages 81–857 and pages 919–949, respectively there is described formation of disalts of $C_{1-4}$ monocarboxylic acids, like potassium diformate and sodium diformate by dissolving pure formates in concentrated and anhydrous formic acid. According to the described laboratory experiments, needle like crystals of diformates etc. are formed. The method for formation of disalts described in Gmelin are only theoretical. Commercial production of such disalts are not reported.

In GB-Patent No. 1.505.388 there is described formation of aqueous solutions of complex salts from ammonium ions and/or ions of a metal selected from Group I and II of the Periodic Table and at least one carboxylic acid. The ratio of acid to ammonium and/or metal ions is in the range of 2:1 and 4:1 on a chemical equivalent basis The concentration of water in the aqueous solution is between 15–75% by weight of the total composition. Said solution of complex salts or disalts of carboxylic acids is stated to be a preservative composition useful in animal feed. This patent does not give any further operating conditions for making the solution of the complex salts and no conditions are given for making dry salts.

The main object of the present invention was to arrive at a new method for the manufacture of products containing disalts of formic acids, where large amounts of the products could be obtained in a form suitable for commercialization.

Another object of the invention was to arrive at products comprising formic acid which were temperature stable i.e. products where the loss of acid was kept at a minimum.

A further object of the invention was to arrive at a crystalline or granulated product which was free-flowing and possessed good storage properties.

Still another object of the invention was to arrive at a product which contains very small amounts of water, and appears with less hygroscopicity compared with the carboxylate itself.

Especially diformates of sodium and potassium were found to have such properties.

It was also an object to produce concentrated solutions or slurries of disalts of formic acid.

By using potassium hydroxide, carbonate, bicarbonate or formate, sodium hydroxide, carbonate, bicarbonate or formate, cesium hydroxide, carbonate, bicarbonate or formate or ammonium formate or ammonia, mixed with formic acid containing 0–30% of water, crystalline diformates were manufactured. The manufactured crystalline diformates were easily separated from the suspension by centrifugation as a filter cake, and the filtrate containing acid salts was collected. The filter cake was transported by a transport belt/bucket conveyor to a drier/mixer. The wet diformate product was dried to a water content <0.2%. Calcium formate or other formates can be added to the drier/mixer. To further dehydrate the diformates, a desiccant can be added to the drier/mixer. Suitable desiccants will be various types of silica, starch etc. One preferred silica desiccant is sold under the tradename Sipernat 50/22 S. The crystalline diformates obtained were free-flowing, dry, stable, i.e. at normal storage temperature (0–80° C.), they did only decompose into acid and formate to a very small degree. Thus the inventor found that by working according to the above concept disalts of formic acid could be made in the following way:

K, Na, Cs or $NH_4$-formate, K, Na, or Cs-carbonate or bicarbonate is mixed with formic acid containing 0–50% water in a reactor at 40–100° C. and reacted to 50–55% of the acid. The mixture is then cooled and the slurry formed is filtered, the filtrate is collected or recirculated and the filter cake containing disalts is transported to a drier/mixer where the disalts are dried. Alternatively other disalts, calcium/magnesium salts and/or a desiccant can be added to the drier/mixer. The filtration is preferably performed by means of a centrifuge.

The preferred mole ratio of K, Na, or $NH_4$-formate and formic acid is 1–1.5:1–1.5. The temperature in the reactor should preferably be between 50–70° C., and the concentration of acid should be in the range 50–100%.

K/Na carbonates/hydroxides can be used in solid form and have a water content of 1–15%.

A preferred process for making Na- or K-diformates can be performed by using only formic acid and NaOH or KOH as raw materials. Optionally Na- or K-carbonates can be used together with the respective hydroxides. This process comprises reacting a 80–95% aqueous solution of formic acid with a solution of 70–80% potassium or sodium formate at 50–60° C. in a first reactor and subsequently cooling the formed mixture to 20–25° C., whereby the formed diformate precipitates. The slurry containing the diformate is separated and the filtrate is transferred to a second reactor where it is reacted with a 50% solution of NaOH or KOH, which optionally may be mixed with the corresponding alkali carbonate. The thus formed formate solution is adjusted to pH 9–10 and then evaporated to a 70–80% solution being transferred to said first reactor. The separated diformate solids are dried by means of air to a water content of <0.2% in a drier.

In an embodiment of the invention, liquid and/or gaseous $NH_3$ or ammonium formate is mixed with formic acid.

In another embodiment crystal masses of Na- and K-disalts are dried at temperatures between 40 and 80° C., preferably between 50 and 70° C.

The new products made according to the above method comprise the following:

Disalts of formic acid containing

20–60% potassium diformate

20–50% sodium di/tetra formate

0–25% calcium mono salt

0–4% desiccant

0–5% water

Another similar product according to the invention contains the following components:

60–99% potassium diformate

0–28% calcium mono salt

0–4% desiccant

0–5% water

A further product is a concentrated solution of disalts of formic acid containing 55–70% diformates.

The scope of the invention is as defined by the attached claims.

The invention is further described and explained in the following description of the figures and the examples which demonstrate manufacture according to the invention.

BRIEF DESCRIPTION OF DRAWINGS

In FIG. 1 the process for manufacture of products containing disalts of formic acid is shown. Potassium hydroxide, carbonate, bicarbonate or formate, sodium hydroxide, carbonate, bicarbonate or formate, cesium hydroxide, carbonate, bicarbonate or formate or ammonium formate or ammonia 1 and 2 is mixed with formic acid 3 in which a small amount of water 4 is added, in a water-cooled agitator reaction tank 5 and 6 at 40–100° C., preferably 50–70° C. The reaction mixture is cooled to 20–40° C. Disalts are precipitated and the slurries 7 and 8 are led into centrifuges 9 and are centrifuged. The filter cakes 11 and 13 containing diformate crystals, are transported on a transport belt/bucket conveyor 14 to a drier/mixer 15. To the drier/mixer 15 additional formates, for instance calcium formate 16 and/or a desiccant 17, can be added. The calcium formate 16 and the desiccant 17 are first led into silos 18 and 19. The product 20 is collected from the drier/mixer 15. The filtrates 10 and 12 are collected from the centrifuge 9. Said filtrates can be applied as such in the form of concentrated solutions containing 55–70% disalts or they can be further processed. The slurries 7 and 8 can be diluted by relinquishment of the filtrate 10 and 12 from the centrifuge 9 to the reaction tank 5 and 6 if desired.

FIG. 2 shows disalts of Na or K by performing the reactions in two reactors 25, 27. In reactor 25 80–95% formic acid 3 is reacted at 50–60° C. with a 70–80% solution 24 of Na/K formate being formed in reactor 27. The resulting solution is cooled to 20–25° C., whereby a coarse crystalline mass of diformate is formed and precipitated. This suspension has a solids content of 40–45% depending on the final temperature during the cooling step. The diformate crystals are removed in a separating device 9, preferably a pusher centrifuge being designed to let crystals having a size below 70 micron get through. The crystal mass will thereby have a $D_{50}$ of about 600 micron. Thus a dust free product is obtained. The filtrate 30 containing diformate in water and small amounts of crystals is pumped to reactor 27 where the acid part is neutralized with a 50% solution of NaOH or KOH 28. A combination of the respective carbonates and a 50% hydroxide solution can also be used. The crystals of the solution will be dissolved during this neutralization. Subsequent to neutralization to pH 9–10, the solution 33 is concentrated in evaporator 26 to which steam 22 can be supplied. The thus concentrated 70–80% solution 24 is transferred to reactor 25. The crystal mass of diformates 32 from the separating device 9 contains about 1–1.5% water and is transferred to a drier 15, which preferably is a paddle drier. In the drier 15 the diformate is dried to a water content <0.2 during 12–18 minutes by air 31 which leaves at 23. The thus dried product 20 can be mixed with a desiccant.

Example 1

Figure 1:
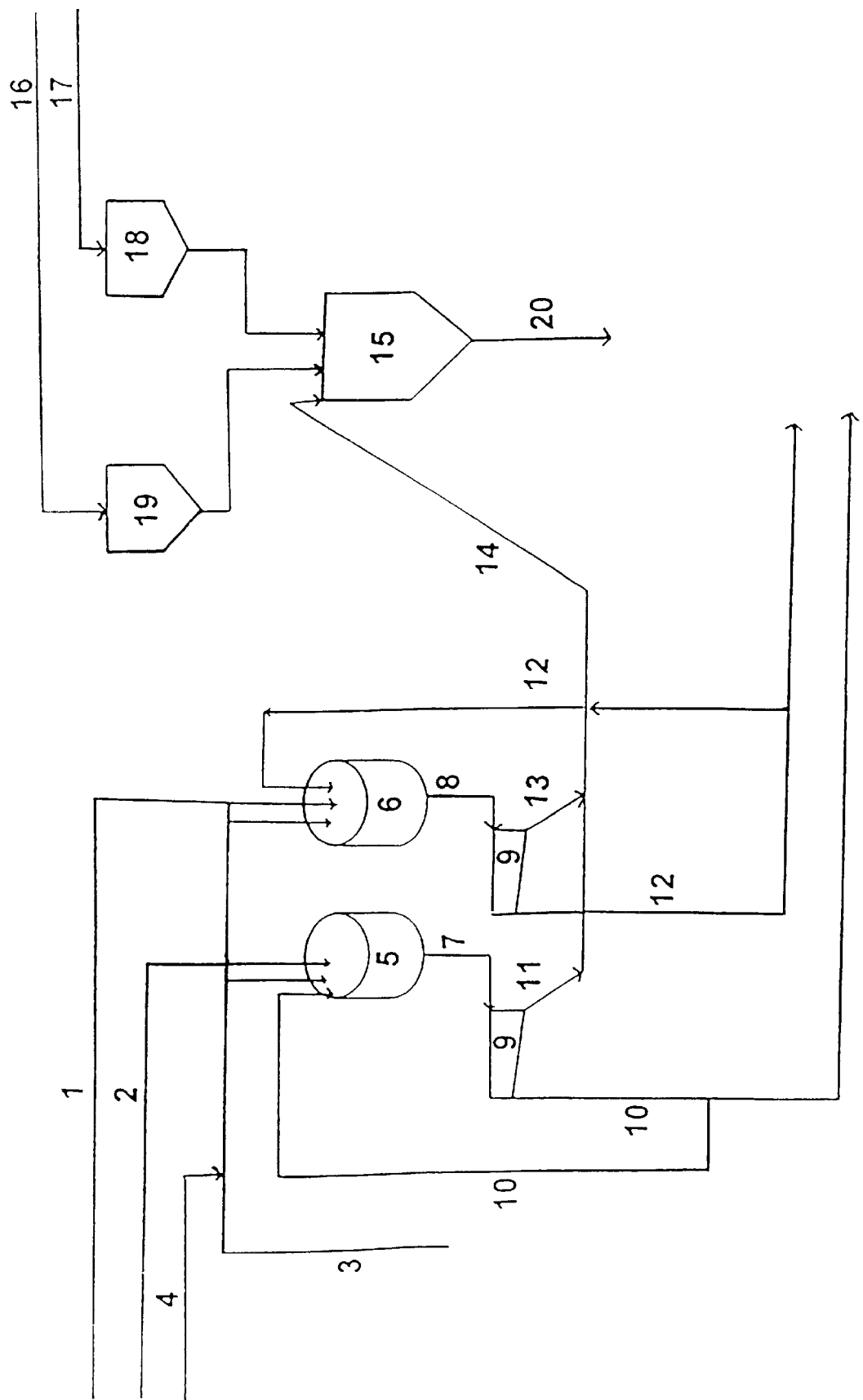
FIG. 1 shows a flow sheet of the process for manufacture of products containing disalts of formic acid.

This example shows manufacture of potassium diformate

91% KOH and 85% formic acid are mixed in a water-cooled agitated reaction tank/crystallizer at 60–70° C. to a conversion of the formic acid of about 50–55%. The reactor is cooled down to 20–40° C. Potassium diformate is precipitated quantitatively and a slurry with about 50–55% dry substance is formed. The slurry is centrifuged continuously to a water content of about 1.5–3% by weight. The filter cake is transported via a transport belt/bucket conveyor to a drier/mixer, and a dry substance with about 0.1% by weight of water is obtained. The content of formic acid is about 35%. Other diformates, dry formates and/or a desiccant can also be added to the drier/mixer. The filtrate collected from the centrifuge can be used to dilute the slurry before centrifugation, if necessary. The collected filtrate can be further processed, i.e. by adding potassium hydroxide to the filtrate the formic acid in the filtrate will be converted to potassium formate solution.

Alternatively the potassium diformate can be manufactured in the same way from 85–95% formic acid and 75% potassium formate.

Example 2

This example shows manufacture of sodium di/tetraformate.

80–90% formic acid is mixed with 97% NaOH dry substance in a water-cooled agitated reaction tank/crystallizer at 60–70° C. to a conversion. of the formic acid of about 50–55%. The reactor is cooled down to 20–40° C., and a mixture of sodium diformate and trisodium tetraformate are quantitatively precipitated and a suspension of about 50% is formed. The suspension is centrifuged to a water content of about 2–5%. The filter cake is transported via a transport belt/bucket conveyor to a drier/mixer. The content in the drier/mixer is dried. The content of formic acid will appear at about 30%. Other diformates, dry formates and desiccant can also be added afterwards to the drier/mixer.

The filtrate collected from the centrifuge can be used to dilute the suspension before centrifugation, if necessary. The filtrate can be further processed in the same way as stated i example 1.

Alternatively the sodium diformate/trisodium tetraformate can be manufactured by dissolving sodium formate in 85–95% formic acid in a mole ratio approximately 1:1. The slurry must be diluted with recirculated filtrate from the centrifugation step. In this case the filter cake is washed continuously with a small amount of diluted NaOH to neutralize the excess acid in the filter cake.

Example 3

This example shows the production of dry, free-flowing products with a high content of potassium diformate and sodium diformate/tetraformate. These types of products are here called Type 1 products.

Potassium diformate and sodium diformate/tetraformate are manufactured as shown in examples 1 and 2. To the drier/mixer calcium formate, a desiccant, a silica product sold under the tradename Sipernat 50/22 S, and water are added. The composition of the mixture in the drier/mixer is:

| Potassium diformate | 49.3% by weight |
|---|---|
| Sodium diformate/tetraformate | 24.6% by weight |
| Calcium formate | 24.6% by weight |
| Desiccant | 1.0% by weight |
| $H_2O$ | 0.5% by weight |

A product of the following total composition based on weight was formed:

| Formic acid | 22.4% |
|---|---|
| Potassium formate | 31.9% |
| Calcium formate | 24.5% |
| Sodium formate | 19.7% |
| Desiccant | 0.5% |
| $H_2O$ | 1.0% |

The product contains about 20% formic acid and about 64.8% formate.

Similar Type 1 products can be manufactured as described in example 3. They will be highly concentrated with regard to total content of formate (propionate etc.) due to the content of disalt of the monocarboxylic acid. Addition of calcium formate/acetate/propionate will depend on the actual use of the Type 1 product The general composition of Type 1 products, when the acid applied is formic acid, will be:

| Potassium diformate | 20–60% |
|---|---|
| Sodium di/tetra-formate | 20–50% |
| Calcium formate | 0–25% |
| Desiccant | 0–4% |
| Water | 0–5% |

The primary application will be as feed additives.

Example 4

This example shows the production of dry, free-flowing products with a high content of potassium diformate. These types of products are here called Type 2 products.

Potassium diformate was manufactured as shown in example 1. To the drier/mixer calcium formate, a desiccant and water are added. The composition of the mixture in the drier/mixer was:

| Potassium diformate | 88.0% by weight |
|---|---|
| Calcium formate | 11.0% by weight |
| Desiccant | 0.5% by weight |
| $H_2O$ | 0.5% by weight |

A product of the following total composition based on weight was formed

| Formic acid | 31.1% |
|---|---|
| Potassium formate | 56.9% |
| Calcium formate | 11.0% |
| Desiccant | 0.5% |
| $H_2O$ | 0.5% |

The product contains about 30% formic acid and about 65.6% formate.

The Type 2 products formed as described above will have the following general composition when the acid applied is formic acid:

| Potassium diformate | 60–99% |
|---|---|
| Calcium formate | 0–28% |
| Water | 0–5% |
| Desiccant | 0–4% |

The primary application will be as feed additives.

Example 5

Figure 2:
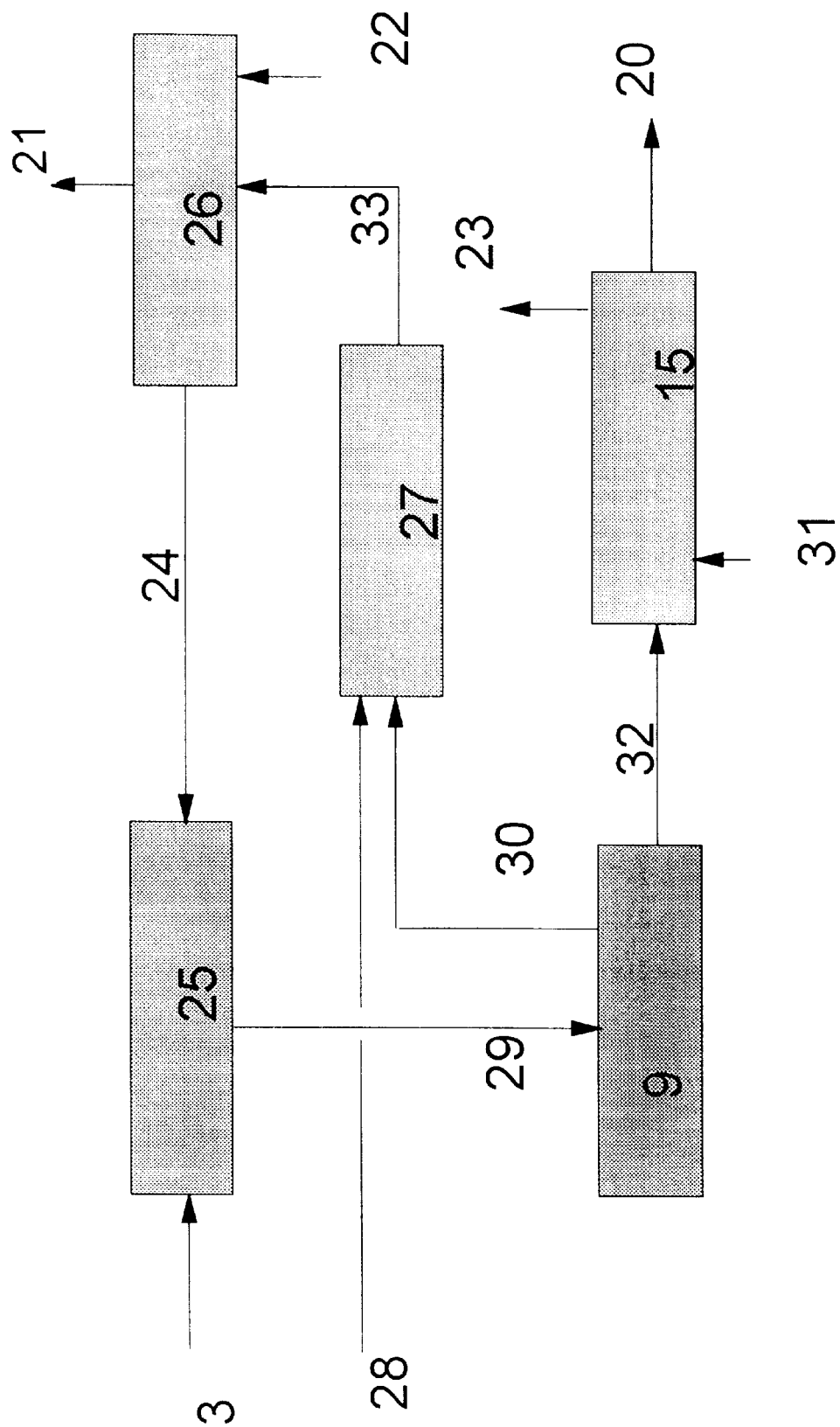
FIG. 2 shows a flow sheet for producing diformates of potassium or sodium.

This example shows preparation of potassium diformate in a process as shown in FIG. 2.

85% formic acid was reacted with a 75% potassium formate in the first reactor 25 at about 55° C. and subsequently cooled to 20–25° C., whereby a coarse crystalline potassium diformate mass was precipitated. The diformate was separated by centrifugation and contained then 1–1.5% water which was further reduced in a drier to <0.2% water. The filtrate containing potassium diformate and small amounts of crystals was pumped to the second reactor 27 where it was reacted with a 50% potassium hydroxide solution, whereby the acid part of the diformate was neutralized. The pH of the solution was adjusted to pH 9–10 and then evaporated to a 75% potassium formate solution which was transferred to reactor 25. The desiccant "Sipernat", a silicon dioxide, was added in amounts of 1-1-3% to the dried potassium diformate.

Sufficient potassium is supplied during the neutralization in the second reactor to give the required mass balance with regard to potassium. Accordingly it is not necessary to supply any external potassium formate to this process, which only requires formic acid and hydroxide which optionally can be mixed with the corresponding alkali carbonate. The finished product was free-flowing and non-dusting and ready for being packed in bags or delivered in bulk.

By the present invention one has arrived at a most flexible and economic process for manufacturing a whole range of highly concentrated products with regard to total content of salts of formic acid, and specifically disalts of formic acid. The main products are dry and free-flowing and possess excellent storage properties, they contain very small amounts of water, and they are temperature stable, i.e. the loss of acid is very small. Also the by-product filtrate, according to the process shown in FIG. 1, can be applied as such or recirculated in the process for manufacture of the main product.

What is claimed is:

1. A method for manufacture of products containing disalts of formic acid, which comprises mixing and reacting K-, Na-, Cs- or $NH_4$-formate; K-, Na- or Cs-hydroxide; K-, Na- or Cs-carbonate; K-, Na- or Cs-bicarbonate; or $NH_3$ with formic acid containing 0–50% water in a reactor at 50–70° C. until approximately 50–55% of the acid is consumed, cooling the mixture to 20–40° C., filtering the slurry thus formed, collecting or recirculating the filtrate, and transferring the filter cake containing disalts to a drier/mixer where the disalts are dried at 40–80° C., to produce a dry, free-flowing and stable product comprising disalts of formic acid.

2. Dry, free-flowing and stable products comprising disalts of formic acid, wherein the general composition of the products is 20–60% potassium disalt, 20–50% sodium di/tetra salt, 0–25% calcium mono salt, 0–4% desiccant, and 0–5% water.

3. Dry, free-flowing and stable products comprising disalts of formic acid, wherein the general composition of the products is 60–99% potassium disalt, 0–28% calcium mono salt, 0–4% desiccant, and 0–5% water.

4. A method for manufacture of products containing disalts of formic acid, which comprises reacting a 80–95% aqueous solution of formic acid with a solution of 70–80% potassium or sodium formate at 50–70° C. in a first reactor, cooling the reaction mixture to 20–25° C. whereby formed diformate precipitates, separating the resultant slurry containing the diformate into a filtrate and solids, transferring the filtrate to a second reactor where it is reacted with a 50% solution of NaOH or KOH, which optionally may be mixed with the corresponding alkali carbonate, adjusting the thus formed formate solution to pH 9–10 and then evaporating the adjusted solution to a 70–80% solution which is transferred to the first reactor, and drying separated diformate solids by means of air to a water content of <0.2% in a drier, wherein approximately 50–55% of the formic acid is consumed in the reactions.

5. A method for manufacture of products containing disalts of formic acid, which comprises reacting liquid and/or gaseous $NH_3$ or ammonium formate with formic acid containing 0–50% water in a reactor at 50–70° C. until approximately 50–55% of the acid is consumed, cooling the mixture to 20–40° C., filtering the slurry thus formed, collecting or recirculating the filtrate, and transferring the filter cake containing disalts to a drier/mixer where the disalts are dried at 40–80° C.

* * * * *